(12) United States Patent
Hancock et al.

(10) Patent No.: US 11,969,208 B2
(45) Date of Patent: Apr. 30, 2024

(54) ELECTROSURGICAL INSTRUMENT FOR PERFORMING ABLATION OR ELECTROPORATION OF BIOLOGICAL TISSUE

(71) Applicant: CREO MEDICAL LIMITED, Chepstow (GB)

(72) Inventors: Christopher Paul Hancock, Bath (GB); John Bishop, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 318 days.

(21) Appl. No.: 16/662,889

(22) PCT Filed: Jun. 1, 2018

(86) PCT No.: PCT/EP2018/064467
§ 371 (c)(1),
(2) Date: Oct. 24, 2019

(87) PCT Pub. No.: WO2018/224404
PCT Pub. Date: Dec. 13, 2018

(65) Prior Publication Data
US 2020/0367965 A1      Nov. 26, 2020

(30) Foreign Application Priority Data
Jun. 8, 2017   (GB) ...................... 1709134

(51) Int. Cl.
*A61B 18/18*   (2006.01)
*A61B 18/00*   (2006.01)
*A61B 18/14*   (2006.01)

(52) U.S. Cl.
CPC ...... *A61B 18/1815* (2013.01); *A61B 18/1492* (2013.01); *A61B 2018/00077* (2013.01);
(Continued)

(58) Field of Classification Search
CPC ............ A61B 18/1815; A61B 18/1853; A61B 18/1861; A61B 2018/0016;
(Continued)

(56) References Cited

U.S. PATENT DOCUMENTS 4,204,549 A      5/1980   Paglione
5,697,882 A *  12/1997   Eggers ................... A61B 18/12
                                                                 604/114
(Continued)

FOREIGN PATENT DOCUMENTS

EP      2 347 727 A1      7/2011
WO      WO-0049957 A1 *   8/2000   ............. A61B 18/14
WO      WO0049957 A1      8/2003

OTHER PUBLICATIONS

British Office Action issued in British Patent Application 1709134.9 dated Dec. 6, 2017.
(Continued)

Primary Examiner — Jaymi E Della
Assistant Examiner — Abigail M Ziegler
(74) *Attorney, Agent, or Firm* — ArentFox Schiff LLP (57) ABSTRACT

An electrosurgical instrument capable of performing both thermal ablation and electroporation in a minimally invasive manner. The instrument is dimensioned to fit within an instrument channel of an endoscope to enable non-percutaneous insertion. The instrument comprises a radiating tip mounted at a distal end of a coaxial transmission line to receive microwave EM energy from the coaxial transmission line and emit it as a field around the radiating tip. The instrument further comprises an auxiliary transmission line arranged to convey electromagnetic energy having an electroporation waveform to a microelectrode array mounted on the radiating tip. The electroporation waveform may be a radiofrequency or low frequency electromagnetic (EM) sig-
(Continued)

nal. The microelectrode array may comprise a plurality of nanoscale conductive electrode elements.

22 Claims, 3 Drawing Sheets (52) U.S. Cl.
CPC ............... *A61B 2018/0016* (2013.01); *A61B 2018/00541* (2013.01); *A61B 2018/00577* (2013.01); *A61B 2018/00613* (2013.01); *A61B 2018/00708* (2013.01); *A61B 2018/00732* (2013.01); *A61B 2018/00982* (2013.01); *A61B 2018/00994* (2013.01); *A61B 2018/1823* (2013.01); *A61B 2018/1853* (2013.01); *A61B 2018/1861* (2013.01)

(58) Field of Classification Search
CPC ............ A61B 2018/00541; A61B 2018/00577; A61B 2018/00613
See application file for complete search history.

(56) References Cited

U.S. PATENT DOCUMENTS

| | | | | |
|---|---|---|---|---|
| 5,788,692 | A * | 8/1998 | Campbell | A61B 18/1815 606/41 |
| 5,800,494 | A | 9/1998 | Campbell et al. | |
| 8,133,222 | B2 * | 3/2012 | Ormsby | A61B 8/12 606/41 |
| 9,179,971 | B2 * | 11/2015 | Kirschenman | G01L 1/005 |
| 9,289,606 | B2 * | 3/2016 | Paul | A61B 18/14 |
| 2005/0113820 | A1 * | 5/2005 | Goble | A61B 18/1206 606/50 |
| 2008/0015570 | A1 * | 1/2008 | Ormsby | A61B 18/1492 606/41 |
| 2010/0004650 | A1 * | 1/2010 | Ormsby | A61B 18/1492 606/41 |
| 2010/0152725 | A1 * | 6/2010 | Pearson | A61B 18/1815 606/41 |
| 2010/0268219 | A1 * | 10/2010 | Ormsby | A61B 18/1815 606/33 |
| 2010/0298761 | A1 * | 11/2010 | Staal | A61N 1/327 604/20 |
| 2011/0237921 | A1 * | 9/2011 | Askin, III | A61B 5/24 607/116 |
| 2012/0203217 | A1 * | 8/2012 | Brannan | A61B 18/1815 606/33 |
| 2013/0046300 | A1 * | 2/2013 | Binmoeller | A61B 1/00131 606/41 |
| 2014/0039489 | A1 * | 2/2014 | Davalos | A61B 18/1477 606/34 |
| 2014/0052118 | A1 | 2/2014 | Laske et al. | |
| 2014/0052119 | A1 * | 2/2014 | Stewart | A61B 18/18 606/33 |
| 2014/0066913 | A1 * | 3/2014 | Sherman | A61B 18/1492 606/41 |
| 2014/0081259 | A1 * | 3/2014 | Deem | A61B 18/1233 606/33 |
| 2014/0121663 | A1 * | 5/2014 | Pearson | A61B 18/1492 606/47 |
| 2014/0243642 | A1 * | 8/2014 | Deac | A61B 5/282 600/374 |
| 2014/0358140 | A1 * | 12/2014 | Emmons | A61N 7/022 606/33 |
| 2014/0364797 | A1 | 12/2014 | Schoenbach et al. | |
| 2016/0051324 | A1 * | 2/2016 | Stewart | A61N 1/327 606/41 |
| 2016/0082180 | A1 * | 3/2016 | Toth | A61M 5/14 604/21 |
| 2016/0113707 | A1 * | 4/2016 | Sahakian | A61B 18/1477 606/41 |
| 2016/0278660 | A1 * | 9/2016 | Nagale | A61B 5/391 |
| 2016/0278851 | A1 * | 9/2016 | Mannion | A61M 25/0147 |
| 2017/0042614 | A1 * | 2/2017 | Salahieh | A61M 25/1011 |
| 2017/0105793 | A1 * | 4/2017 | Cao | A61N 1/325 |
| 2017/0112571 | A1 * | 4/2017 | Thiel | A61B 18/1815 |
| 2017/0156783 | A1 * | 6/2017 | McKernon | A61B 18/1206 |
| 2017/0333109 | A1 * | 11/2017 | Gilbert | A61B 18/1206 |
| 2018/0110562 | A1 * | 4/2018 | Govari | A61M 25/0067 |
| 2018/0214204 | A1 * | 8/2018 | Karmarkar | A61B 18/1815 |

OTHER PUBLICATIONS

International Preliminary Report on Patentability issued in International Patent Application PCT/EP2018/064467 dated May 16, 2019.
International Search Report and Written Opinion issued in an International Patent Application No. PCT/EP2018/064467 dated Sep. 17, 2018.

* cited by examiner

ELECTROSURGICAL INSTRUMENT FOR PERFORMING ABLATION OR ELECTROPORATION OF BIOLOGICAL TISSUE

CROSS-REFERENCE TO RELATED APPLICATIONS

This application is a National Stage entry of International Application PCT/EP2018/064467, filed Jun. 1, 2018, which claims priority to United Kingdom Patent No. GB 1709134.9 filed on Jun. 8, 2017. The disclosure of the priority applications is hereby incorporated in their entirety by reference.

FIELD OF THE INVENTION

The invention relates to an electrosurgical instrument for delivering microwave electromagnetic (EM) energy to treat biological tissue. In particular, the invention relates to an electrosurgical instrument that can be introduced through an instrument channel of a surgical scoping device (e.g. endoscope or bronchoscope) to treat tumours in a minimally invasive manner.

BACKGROUND TO THE INVENTION

It is inherently difficult to gain access to lung tumours due to the small dimensions of the bronchial tree, especially towards the peripheral regions where small nodules are likely to develop. This has resulted in many treatment options being employed such as chemotherapy (targeted medicine, anti-cancer drugs (chemotherapeutic agents)), radiotherapy (delivery of ionizing radiation), surgery (invasive and minimally invasive) and RF/microwave ablation. Surgical procedures involve pneumonectomy (removal of one lung), lobectomy (removal of a lobe), sleeve lobectomy (resection of a lobe along with part of the bronchus that attaches to it), wedge resection (removal of a wedge shaped portion of lung) and segmentectomy/segment resection (resection of a specific lung segment).

It is known to use microwave emitting probes to treat various conditions in the lungs and other body tissues. For example, in the lungs, microwave radiation can be used to treat asthma and ablate tumours or lesions.

Another type of tumour treatment makes use of an effect known as electroporation (or electropermeabilization). In this technique, electrical pulses are applied to biological tissue to cause nanoscale pores to open in cell membranes at a target site. The pores permit anticancer drugs or other material that cannot normally permeate through the cell membrane to enter the cells. The pores may then reseal to trap the material within the cell, where it may cause a therapeutic effect (e.g. to kill the cell).

It is also known to use electroporation to create permanent nanoscale pores in the cell membrane. These pores do not reseal, and thus disrupt cell homeostasis, eventually leading to cell death. This technique is known as irreversible electroporation or non-thermal irreversible electroporation.

Unlike thermal ablation, e.g. using microwave energy, irreversible electroporation preserves the extracellular matrix.

SUMMARY OF THE INVENTION

At its most general, the invention provides an electrosurgical instrument capable of performing both thermal ablation (e.g. using microwave electromagnetic energy) and electroporation (e.g. non-thermal irreversible electroporation) in a minimally invasively manner. The electrosurgical instrument may be conveyed through an instrument channel of a surgical scoping device (e.g. an endoscope, gastroscope, bronchoscope or the like) to enable the instrument to be transported to the treatment site in a non-percutaneous manner.

According to one aspect of the present disclosure, there is provided an electrosurgical instrument for delivering electromagnetic energy to biological tissue at a treatment site, the electrosurgical instrument comprising: a coaxial transmission line comprising an inner conductor, an outer conductor, and a dielectric material separating the inner conductor from the outer conductor, the coaxial transmission line being arranged to convey microwave electromagnetic (EM) energy; a radiating tip mounted at a distal end of the coaxial transmission line to receive the microwave EM energy from the coaxial transmission line and emit the microwave EM energy as a field around the radiating tip; an auxiliary transmission line extending along the coaxial transmission line towards the radiating tip, the auxiliary transmission line being arranged to convey electromagnetic energy having an electroporation waveform; and a microelectrode array mounted on the radiating tip and electrically connected to the auxiliary transmission line, wherein the microelectrode array is configured to receive the electromagnetic energy having an electroporation waveform from the auxiliary transmission line to thereby generate an electric field at the radiating tip for electroporation of biological tissue.

With the above structure, the instrument can be used to selectively perform either ablation with the microwave energy or electroporation with the electric field emitted by the microelectrode array.

The radiating tip may comprise an antenna for emitting the microwave EM energy. For example, the radiating tip may comprise a dielectric cap mounted at the distal end of the coaxial transmission line. The microelectrode array may be mounted on an outer surface of the dielectric cap. The inner conductor of the coaxial transmission line may extend beyond a distal end of the outer conductor, e.g. as a conductive finger, to form a radiating monopole. The dielectric cap may be made of a suitable low loss material, such as ceramic. The dielectric cap may load the coaxial transmission line to enable the antenna to be dimensioned in a manner that is suitable for insertion into an instrument channel of a surgical scoping device.

The auxiliary transmission line may be arranged to convey a radiofrequency or low frequency electromagnetic (EM) signal. In other words, the electromagnetic energy having an electroporation waveform may be a radiofrequency or low frequency electromagnetic (EM) signal. In one example, the auxiliary transmission line may comprise a twisted pair cable.

The coaxial transmission line may carry the auxiliary transmission line within it, e.g. in a longitudinal passage formed therein. For example, the inner conductor of the coaxial transmission line may be hollow to define an longitudinally extending passage. The auxiliary transmission line may extend along the longitudinally extending passage.

The auxiliary transmission line may comprise a first pole conductive element and a second pole conductive element. The electric field for electroporation may be defined by a potential difference between these poles. The microelectrode array may comprise a plurality of electrode elements in electrical contact with one or other of the first pole conductive element or the second pole conductive element. For example, the plurality of electrode elements may be arranged in one or more oppositely poled electrode element pairs. The pairs may be disposed over the surface of the radiating tip. Each pair may create an electric field between its electrode elements to cause electroporation in tissue adjacent to that pair. The electrode elements in each oppositely poled electrode element pair may be spaced from each other at a distance of 0.1 to 0.5 mm.

Each of the plurality of electrode elements may protrude from the surface of the radiating tip. The scale of the protrusion may be very small, e.g. nanoscale, i.e. equal to or less than 100 nm and preferably equal to or less than 10 nm. In one example, each of the plurality of electrode elements may comprise a nanoscale conductive structure, e.g. a carbon nanotube or the like.

The microelectrode array may be fabricated in one or more sheets that wrap around the radiating tip. For example, the one or more sheets may comprise a pair of elastic skins that a stretched to conform to the outer surface of the dielectric cap. Each sheet may have a plurality of electrode elements fabricated or otherwise secured thereon. The electrode elements on each sheet may be electrically interconnected. The electrode elements in each oppositely poled electrode element pair may be on different sheets.

There may be an impedance transformer mounted between the radiating tip and the coaxial transmission line to assist in matching an impedance of the coaxial transmission line to the impedance of the radiating tip.

The coaxial transmission line and the auxiliary transmission line may extend along or within a flexible shaft, e.g. to assist in maneuvering the instrument to a treatment site. In one example, the radiating tip and flexible shaft may be dimensioned to be insertable in to an instrument channel of a surgical scoping device, e.g. an endoscope, gastroscope, bronchoscope, or the like.

In another aspect, the present disclosure provides an electrosurgical apparatus for delivering electromagnetic energy to biological tissue at a treatment site, the apparatus comprising: an electrosurgical generator arranged to output a first signal comprising microwave electromagnetic (EM) energy, and a second signal comprising electromagnetic energy having an electroporation waveform; an electrosurgical instrument as discussed above connected to the electrosurgical generator, wherein the coaxial transmission line is arranged to convey the first signal, and wherein the auxiliary transmission line is arranged to convey the second signal.

The electrosurgical generator may comprise a pulse generator circuit for generating the second signal. In one example, the pulse generator circuit may comprise one or more rapid switching elements (e.g. power MOSFETs) capable of switching ON/OFF a source voltage at the desired frequency.

The pulse generator circuit is arranged to output an electroporation waveform for delivery along the auxiliary transmission line to the microelectrode array. The electroporation waveform may be arranged to enable reversible or irreversible electroporation to be performed at the treatment site. The pulse generator circuit may be controllable, e.g. adjustable by a user, to achieve different electroporation effects. For example, the pulse generator circuit may be adjustable to provide an electroporation waveform having any one or more of: a pulse width in the range from 1 ns to 10 ms, a pulse amplitude in the range of 10 V to 10 kV, and a duty cycle equal to or less than 50%.

In this specification "microwave" may be used broadly to indicate a frequency range of 400 MHz to 100 GHz, but preferably the range 400 MHz to 60 GHz. Specific frequencies that have been considered are: 433 MHz, 915 MHz, 2.45 GHz, 3.3 GHz, 5.8 GHz, 10 GHz, 14.5 GHz and 24 GHz. The device may delivery energy at more than one of these microwave frequencies. The term "radiofrequency" or "RF" may be used to indicate a frequency between 300 kHz and 400 MHz. The term "low frequency" or "LF" may mean a frequency in the range 30 kHz to 300 kHz Herein, the term "inner" means radially closer to the centre (e.g. axis) of the instrument channel. The term "outer" means radially further from the centre (axis) of the instrument channel.

The term "conductive" is used herein to mean electrically conductive, unless the context dictates otherwise.

Herein, the terms "proximal" and "distal" refer to the ends of the energy conveying structure further from and closer to the treatment site respectively. Thus, in use the proximal end is closer to a generator for providing the microwave energy, whereas the distal end is closer to the treatment site, i.e. the patient.

BRIEF DESCRIPTION OF THE DRAWINGS

Embodiments of the invention are discussed below with reference to the accompanying drawings, in which.

DETAILED DESCRIPTION; FURTHER OPTIONS AND PREFERENCES

Figure 1:
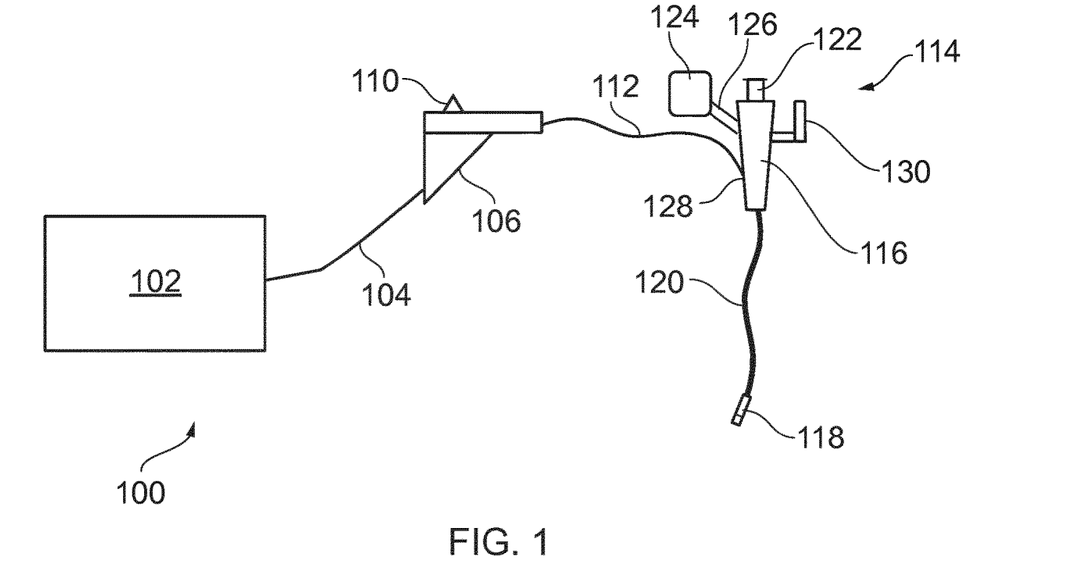
FIG. 1 is a schematic diagram showing a lung ablation system for use with an electromagnetic navigation bronchoscopy apparatus that is an embodiment of the invention.

FIG. 1 is a schematic diagram of a complete electrosurgery system 100 that is capable of supplying microwave energy to the distal end of an invasive electrosurgical instrument. The system 100 comprises a generator 102 for controllably supplying microwave energy, and, in embodiments of this invention energy for electroporation. Energy for electroporation may comprise pulsed or sinusoidal (e.g. continuous wave electromagnetic wave) in the radiofrequency (RF) or low frequency (LF) bands. Herein, reference to RF may mean a frequency in the range of 300 kHz to 300 MHz. Reference to LF may mean a frequency in the range 30 kHz to 300 kHz.

A suitable generator for this purpose is described in WO 2012/076844, which is incorporated herein by reference. The generator may be arranged to monitor reflected signals received back from the instrument in order to determine an appropriate power level for delivery. For example, the generator may be arranged to calculate an impedance seen at the distal end of the instrument in order to determine an optimal delivery power level. The generator may be arranged to deliver power in a series of pulses as discussed below.

The generator 102 is connected to an interface joint 106 by an interface cable 104. If needed, the interface joint 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102 and instrument control mechanism into a single flexible shaft 112, which extends from the distal end of the interface joint 106.

The flexible shaft 112 is insertable through the entire length of an instrument (working) channel of a surgical scoping device 114, such as an endoscope, bronchoscope, gastroscope or the like.

The surgical scoping device 114 comprises a body 116 having a number of input ports and an output port from which an instrument cord 120 extends. The instrument cord 120 comprises an outer jacket which surrounds a plurality of lumens. The plurality of lumens convey various things from the body 116 to a distal end of the instrument cord 120. One of the plurality of lumens is an instrument channel. Other lumens may include a channel for conveying optical radiation, e.g. to provide illumination at the distal end or to gather images from the distal end. The body 116 may include a eye piece 122 for viewing the distal end. In order to provide illumination at the distal end, a light source 124 (e.g. LED or the like) may be connected to the body 116 by an illumination input port 126.

The flexible shaft 112 has a distal assembly 118 (not drawn to scale in FIG. 1) that is shaped to pass through the instrument channel of the surgical scoping device 114 and protrude (e.g. inside the patient) at the distal end thereof. The distal end assembly includes an active tip for delivering microwave energy into biological tissue as discussed herein.

The structure of the distal assembly 118 discussed below may be designed to have a maximum outer diameter equal to or less than 2.0 mm, e.g. less than 1.9 mm (and more preferably less than 1.5 mm) and the length of the flexible shaft can be equal to or greater than 1.2 m.

The body 116 includes a power input port 128 for connecting to the flexible shaft, which comprises a coaxial cable (e.g. a conventional coaxial cable) capable of conveying the microwave energy from the generator 102 to the distal assembly 118, together with an energy conveying means (e.g. a twisted cable pair or the like) for conveying the energy for electroporation. Coaxial cables that are physically capable of fitting down the instrument channel of a surgical scoping device are available with the following outer diameters: 1.19 mm (0.047"), 1.35 mm (0.053"), 1.40 mm (0.055"), 1.60 mm (0.063"), 1.78 mm (0.070"). Custom-sized coaxial cables (i.e. made to order) may also be used.

As discussed above, it is desirable to be able to control the position of at least the distal end of the instrument cord 120. The body 116 may include a control actuator 130 that is mechanically coupled to the distal end of the instrument cord 120 by one or more control wires (not shown), which extend through the instrument cord 120. The control wires may travel within the instrument channel or within their own dedicated channels. The control actuator 130 may be a lever or rotatable knob, or any other known catheter manipulation device. The manipulation of the instrument cord 120 may be software-assisted, e.g. using a virtual three-dimensional map assembled from computer tomography (CT) images.

Figure 2:
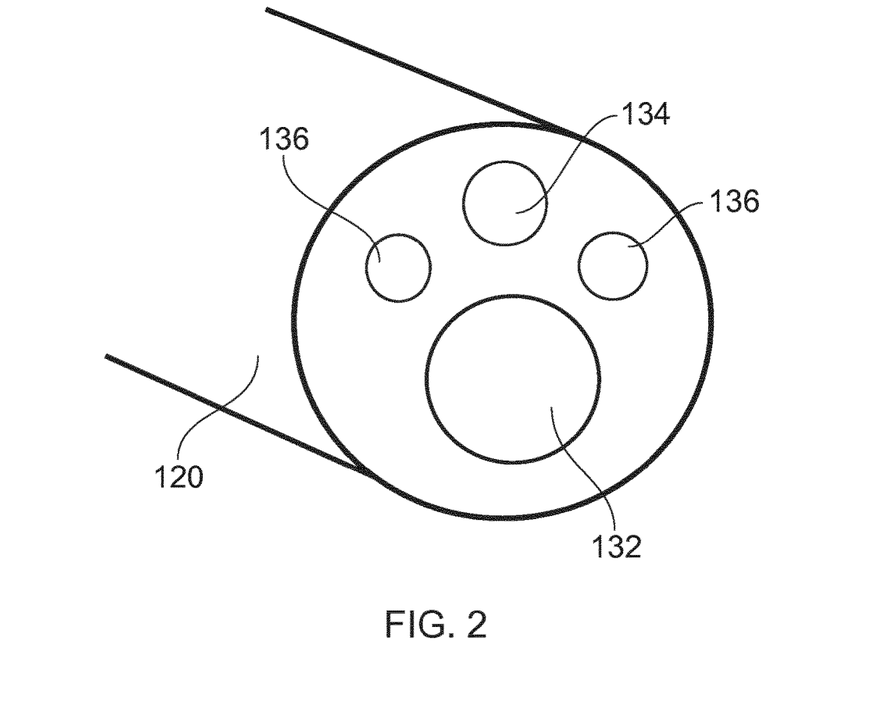
FIG. 2 is a schematic sectional view through an instrument cord of a bronchoscopy instrument cord that can be used with the present invention.

FIG. 2 is a view down the axis of the instrument cord 120. In this embodiment there are four lumens within the instrument cord 120. The largest lumen is the instrument channel 132. The other lumens comprise a camera channel 134 and a pair of illumination channels 136, but the invention is not limited to this configuration. For example, there may be other lumens, e.g. for control wires or fluid delivery or suction.

The invention seeks to provide an instrument that can perform electroporation at the distal end of the instrument channel.

The description below presents a number of energy delivery configurations that are suitable for use in the distal assembly 118 described. Also disclosed are a number of energy delivery profiles. It is to be understood that any of the energy delivery profiles may be used with any of the antenna structures, and that all possible combinations are to be understood as being disclosed.

In the following description, unless stated otherwise, the length of a component refers to its dimension in the direction parallel to the longitudinal axis of the coaxial cable/instrument cord.

Figure 3:
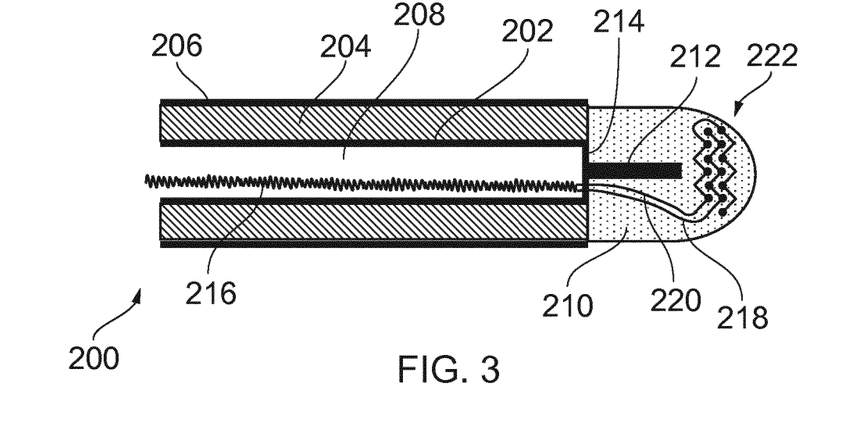
FIG. 3 is a schematic partial cross-section side view through a distal end of an electrosurgical instrument that is an embodiment of the invention.

FIG. 3 is a schematic partial cross-sectional side view of a distal end of an electrosurgical instrument 200 that is an embodiment of the invention. The electrosurgical instrument comprises an longitudinally extending energy conveying structure, which in this example is a flexible coaxial transmission line having a hollow inner conductor in which an auxiliary transmission line for conveying the energy for electroporation is transported. In other examples, the coaxial transmission line and auxiliary transmission line may extend alongside one another, e.g. within a common sleeve or sheath.

The coaxial transmission line comprises a longitudinally extending inner conductor 202, an outer conductor 206 disposed coaxially relative to the inner conductor 202, and a dielectric layer 204 separating the inner conductor 202 from the outer conductor 206. The inner conductor 202 comprises an tube of conductive material defining a longitudinally extending passage 208. The inner conductor 202 may be a conductive layer (e.g. metallised outer surface) of an innermost dielectric conduit (not shown). This structure can facilitate fabrication of the coaxial transmission line and provide electrical isolation between the auxiliary transmission line and the coaxial transmission line.

The auxiliary transmission line in this example is a twisted pair cable 216, i.e. a pair of insulated wire (e.g. copper wire) conductors 218, 220 twisted around each other along the length of the passage 208.

At a distal end of the coaxial transmission line, there is a radiating tip portion for delivering microwave energy received through the coaxial transmission line out of the instrument into the surrounding environment (e.g. biological tissue at a treatment site). In this example, the radiating tip portion comprises a dielectric cap 210 (e.g. made of ceramic or other material that exhibits low loss at the frequencies of microwave energy). The dielectric cap 210 may be a rounded tip, e.g. in the form of a dome. Other shapes can be used, depending on the nature of the treatment site. A conductive finger 212 extends beyond a distal end of the outer conductor 206 of the coaxial transmission line. The conductive finger 212 is electrically connected to the inner conductor 202 and effectively forms an extension to the inner conductor. The conductive finger 212 may be connected to the inner conductor 202 by a radial conductive link 214 that has one or more aperture therein to permit the twisted pair to pass through.

The conductive finger 212 is surrounded by the dielectric cap 210 to form a radiating structure, e.g. monopole antenna, for delivering the microwave energy. Meanwhile, a microelectrode array 222 is formed at an outer surface of the dielectric cap 210 to deliver the energy for electroporation. The microelectrode array 222 comprises a plurality of discrete electrode elements which are alternately connected to different poles of the auxiliary transmission line (i.e. different conductors of the twisted pair). The microelectrode array 222 thus provides a plurality of oppositely poled electrode element pairs. When the electroporation energy is supplied, electric fields are created between each of the oppositely poled electrode element pairs. This arrangement facilitates application of the electric field to biological tissue in the treatment site (i.e. alongside the dielectric cap, whereby electroporation can be performed.

Each of the electrode elements may be protrude from the surface of the dielectric cap 210. This may assist in delivering the electric fields across cells in the biological tissue being treated.

In one example, each electrode element may have a needle-like structure. The electrode element may have a diameter equal to or less than 0.1 mm, e.g. 10 nm. The electrode elements may be carbon nanotubes or other conductive nanoscale structures. The oppositely poled electrode element in each pair may be between 0.05 mm to 0.4 mm apart.

In other examples, the dielectric cap may be configured as a needle, with the electrode elements fabricated on to the outer surface of the needle.

Although not shown in FIG. 3, the instrument may include a stub filter (e.g. one or more stubs) mounted at the distal end of the coaxial transmission line to prevent the microwave energy from leaking into the auxiliary transmission line. Similarly, there may be a capacitor arrangement (e.g. ceramic, microstrip, or waveguide sections with dielectric separating the two) to prevent the electroporation energy (e.g. RF or LF signal) from travelling along the coaxial transmission line. These filtering arrangements may be in the hand piece at the proximal end.

Figure 4:
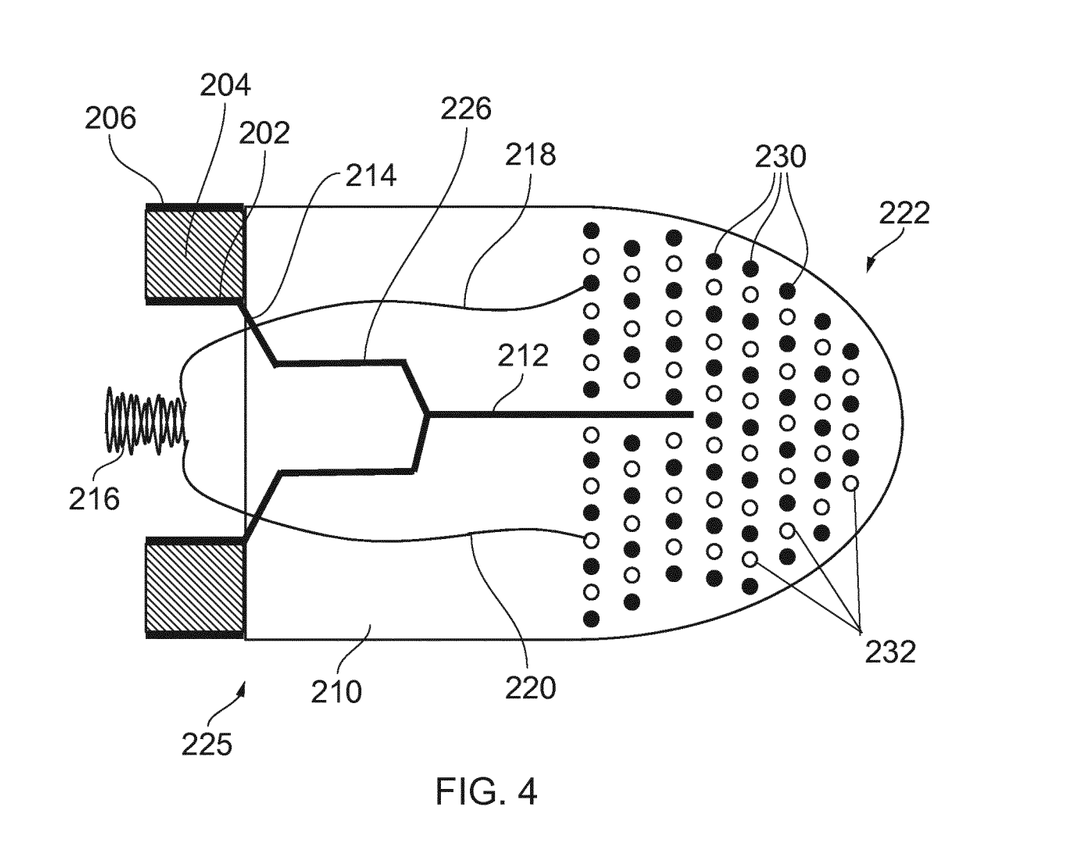
FIG. 4 is a schematic view of a distal tip region of an electrosurgical instrument that is an embodiment of the invention.

FIG. 4 is a schematic view of one example of a distal tip 225 that can be used in the electrosurgical instrument described with reference to FIG. 3. In FIG. 4 the same reference numbers are used for features already described above.

In this example there is an impedance transformer 226 mounted between the conductive finger 212 and the inner conductor 202 to ensure that microwave energy is efficiently delivered out of the radiating tip. As in FIG. 3, the conductive finger 212 is aligned with (e.g. lies on) the axis of the coaxial transmission line, whereby it is encased in the dielectric cap 210. Meanwhile, the microelectrode array 222 comprises a plurality of electrode elements 230, 232 mounted on the outer surface of the dielectric cap 210. A first set of electrode elements 230 are electrically connected to a first pole (conductor) 218 of the auxiliary transmission line 216, while a second set of electrode elements 232 are electrically connected to a second pole (conductor) 220 of the auxiliary transmission line 216. The electrode elements 230, 232 of the first and second sets are mounted in an alternating configuration on the dielectric cap. In this example there are mounted alternately in circumferential rows, but other arrangements are possible. In this configuration, all electrode elements of the first set are at a first common potential (corresponding to the first pole 218), while all the electrode elements of the second set are at a second common potential (corresponding to the second pole 220). Electric fields for electroporation can therefore be created in a quasi-uniform manner over the whole surface of the dielectric cap.

In other examples, the microwave electrode array may be confined to a sub-region of the dielectric cap, so that the location at which the electroporation occurs can be controlled through manipulation (e.g. steering and rotation) of the instrument.

Figure 5A:
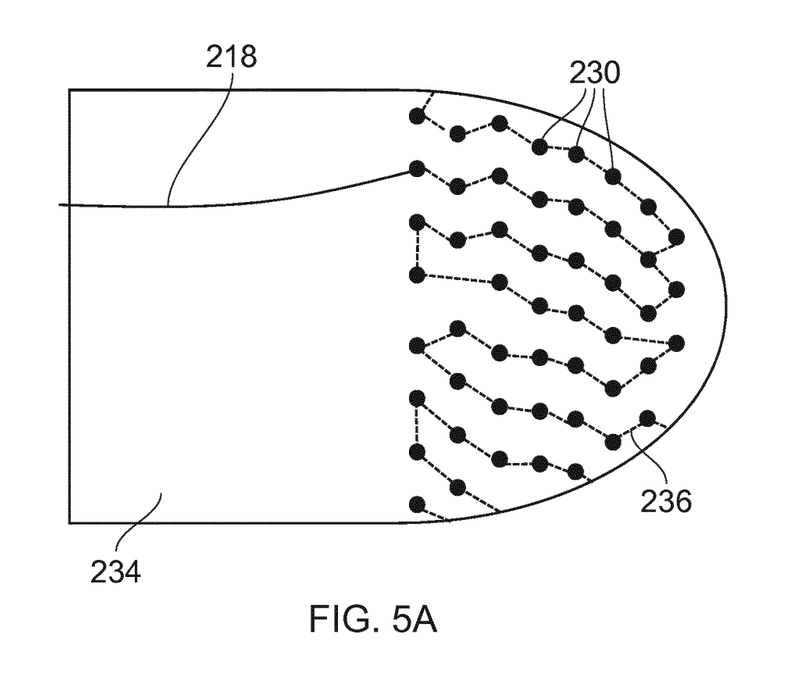
FIG. 5A is a schematic view of a first electrode array skin suitable for use with the instrument of FIG. 4.
Figure 5B:
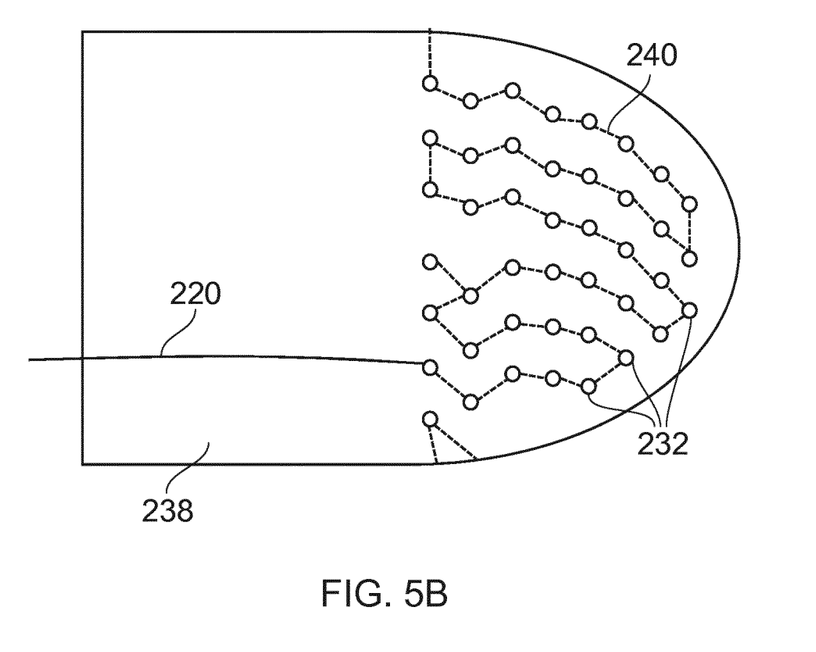
FIG. 5B is a schematic view of a second electrode array skin suitable for use with the instrument of FIG. 4.

FIGS. 5A and 5B are schematic illustrations of two sub-components that may be used to fabricate the radiating tip shown in FIG. 4. Each of FIGS. 5A and 5B depicts an electrode "skin", which is a flexible sheet capable of fitting over and conforming to the surface of the dielectric cap 210. Although FIGS. 5A and 5B depict their skins has having the same shape as the dielectric cap, in practice they may have any suitable shape. For example, they may be a cylindrical sheet of elastic material.

FIG. 5A depicts a first skin 234 which has the first set of electrode elements 230 fabricated, e.g. deposited or otherwise mounted or affixed, thereon. The electrode elements 230 may be interconnected by suitable conductive links 236, e.g. metallisation strips or the like. The electrode elements may be connected in series as shown in FIG. 5A or by an network of interconnections.

FIG. 5B depicts a second skin 238 which has the second set of electrode elements 232 fabricated thereon. The electrode elements 232 are interconnected by conductive links 236.

The first set of electrode elements 230 on the first skin 234 are electrically connected to a first pole 218 of the auxiliary transmission line. The second set of electrode elements 232 on the second skin 238 are electrically connected to a second pole 220 of the auxiliary transmission line. The first and second skins 234, 238 may be mounted one over the other on the dielectric cap to form a radiating tip with means for delivering energy for electroporation.

The energy for electroporation is essentially RF or low frequency (LF) high voltage pulses or bursts of sinusoidal energy configured to open pores in cell membranes. The instrument of the invention may be used in scenario where a therapeutic agent in present in the treatment site, whereby open pores in the cell membrane facilitates or enables the therapeutic agent to enter the cells. In other words, the instrument may be used in conventional electroporation procedures.

Alternatively or additionally, the energy for electroporation may be configured to permanently open pores, thereby to cause irreversible disruption to the cell membrane causing the cells to die. In other words, the instrument can be used for irreversible electroporation (IRE).

In order to provide the energy for electroporation, the generator may comprise a pulse generator circuit for generating a pulsed or otherwise amplitude varying electrical signal. In one example, the pulse generator circuit may output a continuous wave (e.g. sinusoidal signal) in one or more discrete bursts. In another example, the pulse generator circuit may comprise one or more rapid switching elements (e.g. MOSFET transistors) capable of switching ON/OFF a drain-source voltage at the desired frequency for the electroporation energy. For example, the pulse generator circuit may be based on high voltage ($V_{DS}$max>1 kV) power MOSFETs in a push-pull arrangement. In order to charge up the gate-source capacitance and gate-drain capacitances fast enough, the pulse generator circuit may include gate drivers that can source high enough current to charge up the input capacitances.

In one example, the pulse generator circuit operates from a ground potential (0 V) and produces positive pulses using two 1.7 kV MOSFETs in a push-pull arrangement in order to achieve a fast turn-on/turn off rate of around 900V/50 ns.

The pulse generator circuit may output an electroporation waveform for delivery along the auxiliary transmission line to the microelectrode array.

The electroporation waveform may have a pulse width in the range from 1 ns to 10 ms, although the invention need not be limited to this range. Shorter duration pulses (e.g. equal to or less than 10 ns) may be preferred for reversible electroporation. Preferably the rise time of each pulse is equal to or less than 90% of the pulse duration, more preferably equal to or less than 50% of the pulse duration, and most preferably equal to or less than 10% of the pulse duration. For the shorter pulses, the rise time may be of the order of 100 ps.

The electroporation waveform may have a pulse amplitude in the range of 10 V to 10 kV, although the invention need not be limited to this range. With this arrangement, the instrument may be able to provide an electric field amplitude of up to 2 kV/cm (20 kV/mm) between the oppositely poled electrode element pairs.

The electroporation waveform may be a single pulse or a plurality of pulses, e.g. a period train of pulses. The waveform may have a duty cycle equal to or less than 50%, e.g. in the range 0.5% to 50%.

As mentioned above, the waveform can be sinusoidal or discrete (e.g. square wave or the like). The pulses may be positive pulses from a ground potential, or a sequence of alternating positive and negative pulses from a ground potential.

The electroporation energy may be delivered during a treatment period that is selected depending on the desired effect. For example, the treatment period may be short, e.g. less than 1 second, or a few seconds, or around 1 minute. Alternatively the treatment period may be longer, e.g. up to an hour.

For irreversible electroporation, longer duration pulses or more pulses may be used relative to reversible electroporation. For example, pulse widths of the order of 200 ms delivered in a series of 10 to 100 pulses may be used for irreversible electroporation. In one example, the electroporation waveform may comprise 10×300 μs pulses of amplitude 1.5 kV/cm (150 V/mm) delivered three times with around 1 minute between delivery. This waveform can cause cell apoptosis or death in hepatocellular carcinoma.

The pulse generator circuit may be controllable to adapt or vary the electroporation waveform to suit the desired treatment. Thus, any of the duty cycle, pulse width and pulse amplitude may be adjustably variable.

The instrument disclosed herein may be suitable for delivering a combination of microwave energy and energy for electroporation to a variety of different treatment sites. For example, the instrument may be used to treat tumours in the lung, gastrointestinal tract, brain, pancreas, and the like. The electroporation energy may be suitable for cell neutralization of glioblastoma and medulloblastoma.

The ability to perform irreversible electroporation may provide the instrument with a tissue treatment modality that is focussed at the distal tip. This may in turn permit the microwave ablation modality to be used to treat a larger volume around the distal tip. In combination, the instrument can be controlled to select the volume of tissue to which energy is delivered.

In one example, the microwave energy may have a frequency at a lower end of the microwave range, e.g. 433 MHz or the like. An advantage of using energy at this frequency is that losses along the coaxial transmission line can be reduced, which avoid unwanted heating of tissue around the instrument channel away from the treatment site.

In another example, the microelectrode array may be incorporated into an existing needle-based instrument used for endoscopic retrograde cholangio-pancreatography (ERCP). In this example, the microelectrode array may comprise a single electrode pair or an array of very small diameter electrodes incorporated into the needle to enable irreversible electroporation to be used as means for killing cancer cells.

This device may also be adapted to deliver microwave energy. For example a coaxial transmission line may be formed around the existing needle-based instrument, e.g. by coating it in a conductive material (such as Ag), wrapping a dielectric layer over the conductive material and then wrapping a conductive (e.g. Ag) tape layer over that. A biocompatible sleeve (e.g. a heat shrink layer) may be finally applied to secure the structure. In this arrangement, an existing needle-based instrument can thus be adapted to provide either or both of an irreversible electroporation functionality and a microwave ablation functionality.

The invention claimed is:

1. An electrosurgical instrument for delivering microwave electromagnetic (EM) energy and for delivering EM energy having an electroporation waveform to biological tissue at a treatment site, the electrosurgical instrument comprising:
   a coaxial transmission line comprising an inner conductor, an outer conductor, and a dielectric material separating the inner conductor from the outer conductor, the coaxial transmission line being arranged to convey the microwave EM energy;
   a radiating tip mounted at a distal end of the coaxial transmission line and configured to receive the microwave EM energy from the coaxial transmission line and configured to emit the microwave EM energy as a field around the radiating tip;
   an auxiliary transmission line extending along the coaxial transmission line towards the radiating tip, the auxiliary transmission line being arranged to convey the EM energy having the electroporation waveform; and
   a microelectrode array mounted on the radiating tip and electrically connected to the auxiliary transmission line,
   wherein the microelectrode array is configured to receive the EM energy having the electroporation waveform from the auxiliary transmission line to thereby generate an electric field at the radiating tip for electroporation of the biological tissue;
   wherein the auxiliary transmission line comprises a first pole conductive element and a second pole conductive element, and wherein the microelectrode array comprises a first subset of electrodes in electrical contact with the first pole conductive element and a second subset of electrodes in electrical contact with the second pole conductive element;
   wherein the microelectrode array is configured to be secured on a first sheet and a second sheet, wherein the first sheet and the second sheet wrap around the radiating tip;
   wherein the radiating tip comprises a dielectric cap mounted at the distal end of the coaxial transmission line, and wherein the microelectrode array is mounted on an outer surface of the dielectric cap;
   wherein the first and second sheets are mounted one over the other with a top surface of the first sheet directly contacting a bottom surface of the second sheet on the dielectric cap; wherein the first sheet comprises the first subset of electrodes, and the second sheet comprises the second subset of electrodes.

2. An electrosurgical instrument according to claim 1, wherein the inner conductor of the coaxial transmission line extends beyond a distal end of the outer conductor as a conductive finger to form a radiating antenna structure.

3. An electrosurgical instrument according to claim 1, wherein the EM energy having the electroporation waveform is a radiofrequency or low frequency EM signal.

4. An electrosurgical instrument according to claim 1, wherein the auxiliary transmission line comprises a twisted pair cable.

5. An electrosurgical instrument according to claim 1, wherein the inner conductor of the coaxial transmission line is hollow to define a longitudinally extending passage, and wherein the auxiliary transmission line passes though the longitudinally extending passage.

6. An electrosurgical instrument according to claim 1, wherein a plurality of electrodes of the microelectrode array are arranged in one or more oppositely poled electrode pairs.

7. An electrosurgical instrument according to claim 6, wherein each electrode of the one or more oppositely poled electrode pairs in each oppositely poled electrode pair are spaced from each other at a distance of 0.1 to 0.5 mm.

8. An electrosurgical instrument according to claim 1, wherein each electrode of the microelectrode array protrude from a surface of the radiating tip.

9. An electrosurgical instrument according to claim 1, wherein each electrode of the microelectrode array is a nanoscale conductive structure having at least one dimension equal to or less than 100 nm.

10. An electrosurgical instrument according to claim 1 including an impedance transformer mounted between the radiating tip and the coaxial transmission line.

11. An electrosurgical instrument according to claim 1, wherein the coaxial transmission line and the auxiliary transmission line extend along or within a flexible shaft.

12. An electrosurgical apparatus for delivering microwave electromagnetic (EM) energy and for delivering EM energy having an electroporation waveform to biological tissue at a treatment site, the electrosurgical apparatus comprising:
  an electrosurgical generator arranged to output a first signal comprising the microwave EM energy, and a second signal comprising the EM energy having the electroporation waveform;
  the electrosurgical instrument according to claim 1 connected to the electrosurgical generator,
  wherein the coaxial transmission line is arranged to convey the first signal, and
  wherein the auxiliary transmission line is arranged to convey the second signal.

13. An electrosurgical apparatus according to claim 12, wherein the electrosurgical generator comprises a pulse generator circuit for generating the second signal.

14. An electrosurgical apparatus according to claim 13, wherein the pulse generator circuit comprises one or more rapid switching elements capable of switching ON/OFF a source voltage at a selected frequency.

15. An electrosurgical apparatus according to claim 14, wherein the one or more rapid switching elements comprise a pair of power MOSFETs in a push-pull configuration.

16. An electrosurgical apparatus according to claim 13, wherein the pulse generator circuit is arranged to output the electroporation waveform for delivery along the auxiliary transmission line to the microelectrode array, wherein the electroporation waveform has any one or more of:
  a pulse width in the range from 1 ns to 10 ms,
  a pulse amplitude in the range of 10 V to 10 kV, or
  a duty cycle equal to or less than 50%.

17. An electrosurgical apparatus according to claim 12 further comprising a surgical scoping device, wherein the electrosurgical instrument dimensioned to be insertable into an instrument channel of the surgical scoping device.

18. An electrosurgical instrument according to claim 9, wherein the at least one dimension is equal to or less than 10 nm.

19. An electrosurgical instrument according to claim 1, wherein the first and second sheets are each a flexible sheet capable of fitting over and conforming to the outer surface of the dielectric cap.

20. An electrosurgical instrument according to claim 1, wherein the first sheet and the second sheet are elastic skins that are mounted to the dielectric cap by being stretched to conform to the outer surface of the dielectric cap.

21. An electrosurgical instrument according to claim 1, wherein the dielectric cap is formed of a material that exhibits low loss at frequencies of microwave energy such that the microwave energy can radiate through the dielectric cap to the biological tissue at the treatment site.

22. An electrosurgical instrument according to claim 2, wherein the dielectric cap is a hollow cap which surrounds the conductive finger to form the radiating antenna structure.

* * * * *